(12) United States Patent
Bruening

(10) Patent No.: US 10,202,332 B2
(45) Date of Patent: Feb. 12, 2019

(54) METHOD FOR PREPARING 2-AMINO-N-(2,2,2-TRIFLUOROETHYL) ACETAMIDE

(75) Inventor: Joerg Bruening, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 13/824,309

(22) PCT Filed: Sep. 23, 2011

(86) PCT No.: PCT/US2011/052938
§ 371 (c)(1),
(2), (4) Date: Jun. 24, 2013

(87) PCT Pub. No.: WO2012/047543
PCT Pub. Date: Apr. 12, 2012

(65) Prior Publication Data
US 2013/0267729 A1    Oct. 10, 2013

Related U.S. Application Data

(60) Provisional application No. 61/386,673, filed on Sep. 27, 2010.

(51) Int. Cl.
| C07C 261/00 | (2006.01) |
| C07C 231/02 | (2006.01) |
| C07C 231/12 | (2006.01) |
| C07C 231/14 | (2006.01) |

(52) U.S. Cl.
CPC .......... *C07C 231/02* (2013.01); *C07C 231/12* (2013.01); *C07C 231/14* (2013.01); *Y02P 20/55* (2015.11)

(58) Field of Classification Search
CPC ... C07C 231/02; C07C 231/12; C07C 231/14; C07C 237/22; C07C 237/06; Y02P 20/55
USPC ............................................. 560/31; 564/139
See application file for complete search history.

(56) References Cited

U.S. PATENT DOCUMENTS

| 4,484,001 A | * | 11/1984 | Krogh | C07C 237/00 530/337 |
| 5,110,797 A | * | 5/1992 | Ienaga | C07D 207/16 514/17.7 |
| 5,952,497 A | * | 9/1999 | Carey | C07C 271/22 544/183 |
| 6,031,127 A | * | 2/2000 | Yamamoto | C07F 5/025 549/213 |
| 2003/0190348 A1 | * | 10/2003 | Kumar | A61K 9/1272 424/450 |

FOREIGN PATENT DOCUMENTS

| CA | 2730405 | | 1/2010 |
| JP | 2009-173621 | * | 8/2009 |
| JP | 2009173621 | | 8/2009 |
| WO | 2006095014 | | 9/2006 |
| WO | WO 2006/095014 | * | 9/2006 |

(Continued)

OTHER PUBLICATIONS

JP2009-173621 translation 2009.*

(Continued)

*Primary Examiner* — Yevgeny Valenrod
*Assistant Examiner* — Blaine G Doletski

(57) ABSTRACT

Disclosed are methods for preparing compounds of Formula 1 and 1A. The first method utilizes a benzyl carbamate amine protecting group and an intermediate of Formula 4. The second method utilizes a tert-butyl carbamate amine protecting group and an intermediate of Formula 7. The third method utilizes a dibenzyl amine protecting group. Also disclosed is a compound, phenylmethyl N-[2-oxo-2-[(2,2,2-trifluoroethyl)amino]ethyl]carbamate (a compound of Formula 4). Further disclosed is a method for preparing a compound of Formula 14 from a compound of Formula 15 and a compound of Formula 1 or 1A.

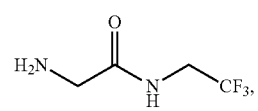

1

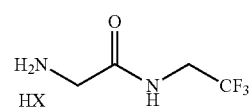

1A

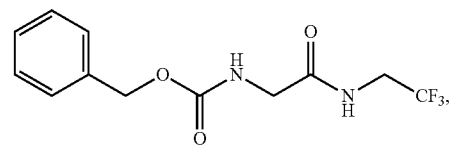

4

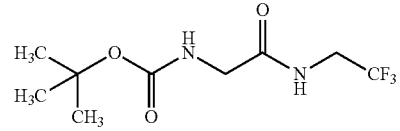

7

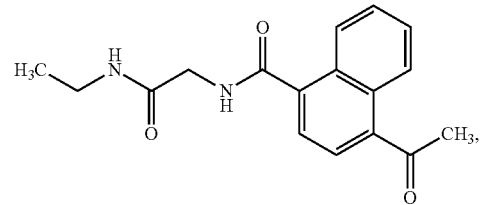

14

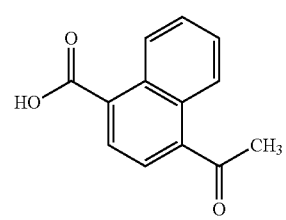

15

5 Claims, No Drawings

(56) References Cited

FOREIGN PATENT DOCUMENTS

| WO | WO2006095014 | * | 9/2006 |
|----|--------------|---|--------|
| WO | 2009025983 | | 2/2009 |
| WO | 2009126668 | | 10/2009 |
| WO | 2010070068 | | 6/2010 |
| WO | WO2010/070068 | * | 6/2010 |
| WO | WO2011037947 | * | 3/2011 |

OTHER PUBLICATIONS

Montalbetti et al. (Amide Bond Dormation and peptide Coupling, Tetrahedron 61 10827-10852, 2005).*
Han et al. (Recent development of peptide coupling reagents in organic synthesis, Tetrahedron 60 (2004) 2447-2467).*
Peptide Guide 2008.*
Green 1999, 1 page.*
Weisenburger et al. (Pilot-Plant Preparation of an αvβ3 Integrin Antagonist: Process Development of a Carbonyldiimidazole Peptide Coupling Organic Process Research & Development, 13, 60-63, published 2009).*
Solvent Substitutions published pp. 1-3 (2009).*
Harada et al., "2-Alkynyl-8-aryladenines possessing an amide moiety: their synthesis and structure-activity relationships of effects on hepatic glucose production induced via agonism of the A(2B) adenosine receptor," Bioorganic and Medicinal Chemistry (2001) 9(10):2709-2726.
Janda et al., "Syntheses of the Saturated Analogues of 4-Nitrophenol and 4-Nitroaniline," Synthetic Communications (1990) 20:1073-1082.
Lesk et al., "Acetyl Bromide-Alcohols as Convenient Reaction Systems for: a) Removal of N-tert-Boc, N-Cbz and N-Ac Protective Groups, b) Esterifications and Transesterifications, c) Debenzylation of Aryl-O-Benzyl Ethers," Synthetic Communications (1999) 28:1405-1408.
Feist "Neue Synthesen aromatischer Acetyl-carbonsäuren and Polycarbonsauren," Justus Liebigs Annalen der Chemie (1932) 496:99-122.

* cited by examiner

METHOD FOR PREPARING 2-AMINO-*N*-(2,2,2-TRIFLUOROETHYL)ACETAMIDE

CROSS-REFERENCE TO RELATED APPLICATIONS

This application is the U.S. National Stage filing of International Application Serial No. PCT/US11/052938 filed Sep. 23, 2011, which claims priority to U.S. Provisional Application No. 61/386,673 filed Sep. 27, 2010, each of which is incorporated herein by reference in its entirety.

FIELD OF THE INVENTION

This invention pertains to a method for preparing 2-amino-N-(2,2,2-trifluoroethyl)acetamide and its salts. The present invention also relates to intermediates for the aforedescribed method and use of the subject compound as a starting material in other preparative methods.

SUMMARY OF THE INVENTION

The present invention provides a method for preparing a compound of Formula 1

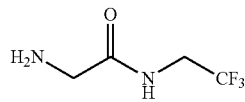

1 comprising (A) contacting a compound of Formula 2

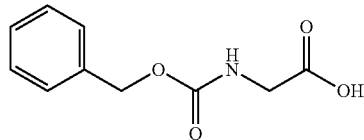

2 with a compound of Formula 3

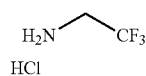

3 and a coupling reagent to form an intermediate of Formula 4 in the presence of a base

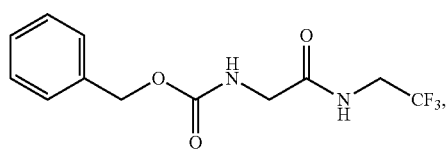

4

(B) contacting the intermediate of Formula 4 with hydrogen in the presence of a hydrogenolysis catalyst to give a compound of Formula 1, and (C) optionally contacting the compound of Formula 1 with an acid of Formula 5

HX    5 wherein X is Cl, Br, $CF_3CO_2$, $CH_3SO_3$, $(SO_4)_{1/2}$ or $(PO_4)_{1/3}$
to provide the compound of Formula 1 in HX salt form (i.e. Formula 1A).

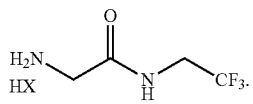

1A

The present invention also relates to novel compound phenylmethyl N-[2-oxo-2-[(2,2,2-trifluoroethyl)amino]ethyl]carbamate (a compound of Formula 4) useful as an intermediate for the aforedescribed method.

The present invention also provides a method for preparing a compound of Formula 1A

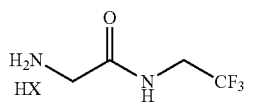

1A wherein X is Cl, Br, $CF_3CO_2$, $CH_3SO_3$, $(SO_4)_{1/2}$ or $(PO_4)_{1/3}$.
comprising (A1) contacting a compound of Formula 8

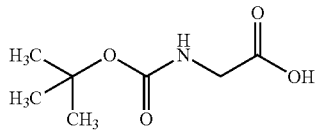

8 with a compound of Formula 3

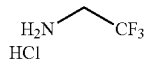

3 and a coupling reagent to form an intermediate of Formula 7 in the presence of a base

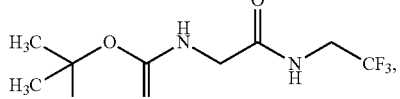

7 and (B1) contacting the intermediate of Formula 7 with an acid of Formula 5

HX.    5

The invention also provides a method for preparing a compound of Formula 14 comprising contacting a compound of Formula 15

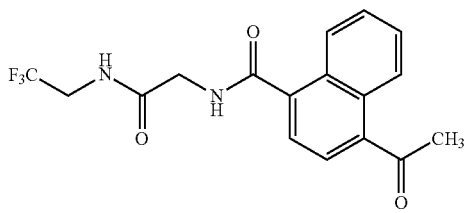

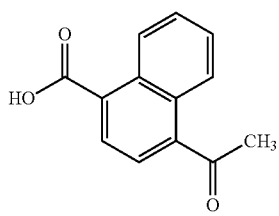

with a compound of Formula 1 or 1A

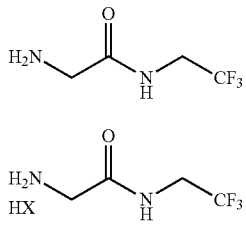

wherein X is Cl, Br, CF$_3$CO$_2$, CH$_3$SO$_3$, (SO$_4$)$_{1/2}$ or (PO$_4$)$_{1/3}$
and a coupling reagent in the presence of a base.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "coupling reagent" refers to a reagent used to activate a carboxylic acid functional group to facilitate its condensation with an amine functional group to form an amide bond.

A compound of Formula 1 in HX salt form is a compound of Formula 1A

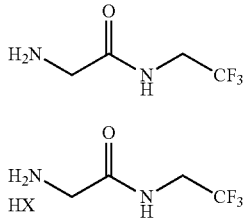

wherein X is Cl, Br, CF$_3$CO$_2$, CH$_3$SO$_3$, (SO$_4$)$_{1/2}$ or (PO$_4$)$_{1/3}$.

The compound of Formula 1A is meant to represent a salt of the compound of Formula 1 and it can be alternatively depicted as Formula 1AA shown below:

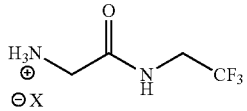

wherein X is Cl, Br, CF$_3$CO$_2$, CH$_3$SO$_3$, (SO$_4$)$_{1/2}$ or (PO$_4$)$_{1/3}$.

When the X is indicated to be (SO$_4$)$_{1/2}$ it is meant sulfuric acid forms a sulfate salt with the compound of Formula 1 as shown below; wherein the two structures correspond respectively to Formula 1AA and Formula 1A.

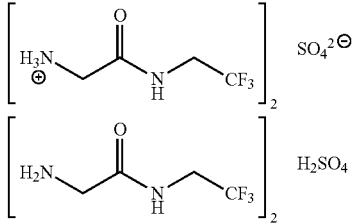

A compound of Formula 1 is 2-amino-N-(2,2,2-trifluoroethyl)acetamide. A compound of Formula 1A is 2-amino-N-(2,2,2-trifluoroethyl)acetamide hydrochloride. A compound of Formula 4 is phenylmethyl N-[2-oxo-2-[(2,2,2-trifluoroethyl)amino]ethyl]carbamate. A compound of Formula 14 is 4-acetyl-N-[2-oxo-2-[(2,2,2-trifluoroethyl)amino]ethyl]-1-naphthalene-carboxamide.

Embodiments of the present invention include:

Embodiment 1.0

The method described in step (A) of the Summary of the Invention wherein the compounds of Formulae 2 and 3 and the coupling reagent are contacted in the presence of a base and a water immiscible solvent.

Embodiment 1.1

The method of Embodiment 1.0 wherein the water immiscible solvent comprises ethyl acetate or iso-propyl acetate.

Embodiment 1.2

The method of Embodiment 1.1 wherein the water immiscible solvent comprises ethyl acetate.

Embodiment 1.3

The method described in step (A) of the Summary of the Invention or any one of Embodiments 1.0 through 1.3 wherein the coupling reagent comprises iso-butyl chloroformate or N,N'-carbonyldiimidazole.

Embodiment 1.4

The method of Embodiment 1.3 wherein the coupling reagent comprises N,N'-carbonyldiimidazole.

Embodiment 1.5

The method described in step (A) of the Summary of the Invention or any one of Embodiments 1.0 through 1.4 wherein the base comprises a basic reagent other than a compound derived from the coupling reagent.

Embodiment 1.6

The method of Embodiment 1.5 wherein the basic reagent comprises triethylamine or N,N-diisopropylethylamine.

Embodiment 1.7

The method of Embodiment 1.6 wherein the basic reagent comprises triethylamine.

Embodiment 1.8

The method described in step (A) of the Summary of the Invention or any one of Embodiments 1.0 through 1.7 wherein the base is derived from the coupling reagent and the coupling reagent is N,N'-carbonyldiimidazole.

Embodiment 1.9

The method described in step (A) of the Summary of the Invention or any one of Embodiments 1.0 through 1.8 wherein the compound of Formula 2 is first contacted with the coupling reagent to form a mixture (i.e. containing the acyl imidazole of Formula 6) and then the compound of Formula 3 is added to the mixture in the presence of base.

Embodiment 1.10

The method described in step (A) of the Summary of the Invention or any one of Embodiments 1.0 through 1.9 wherein the mixture is at a temperature of at least about 15° C.

Embodiment 1.11

The method described in step (A) of the Summary of the Invention or any one of Embodiments 1.0 through 1.10 wherein the mixture is at a temperature of no more than about 40° C.

Embodiment 1.12

The method described in step (A) of the Summary of the Invention or any one of Embodiments 1.0 through 1.11 wherein the molar ratio of the coupling reagent to the compound of Formula 2 is about 1.0 to about 1.1.

Embodiment 1.13

The method described in step (A) of the Summary of the Invention or any one of Embodiments 1.0 through 1.12 wherein the molar ratio of the compound of Formula 3 to the compound of Formula 2 is about 1.0.

Embodiment 1.14

The method described in step (B) of the Summary of the Invention wherein the compound of Formulae 4 and hydrogen are contacted in the presence of a hydrogenolysis catalyst and a water immiscible solvent.

Embodiment 1.15

The method of Embodiment 1.14 wherein the water immiscible solvent comprises ethyl acetate or iso-propyl acetate.

Embodiment 1.16

The method of Embodiment 1.15 wherein the water immiscible solvent comprises ethyl acetate.

Embodiment 1.17

The method described in step (B) of the Summary of the Invention or any one of Embodiments 1.14 through 1.16 wherein the hydrogenolysis catalyst is a precious metal catalyst or a supported precious metal catalyst.

Embodiment 1.18

The method of Embodiment 1.17 wherein the hydrogenolysis catalyst is palladium on carbon.

Embodiment 1.19

The method of Embodiment 1.18 wherein the hydrogenolysis catalyst is 5% or 10% palladium on carbon.

Embodiment 1.20

The method described in step (B) of the Summary of the Invention or any one of Embodiments 1.14 through 1.19 wherein the hydrogenolysis is carried out at ambient temperature.

Embodiment 1.21

The method described in step (B) of the Summary of the Invention or any one of Embodiments 1.14 through 1.20 wherein the hydrogenolysis is carried out at a pressure of atmospheric pressure to about 50 psi.

Embodiment 1.22

The method of Embodiment 1.21 wherein the hydrogenolysis is carried out at atmospheric pressure.

Embodiment 1.23

The method described in step (C) of the Summary of the Invention wherein the compound of Formula 1 is contacted with an acid of Formula 5 in the presence of a water immiscible solvent.

Embodiment 1.24

The method of Embodiment 1.23 wherein the water immiscible solvent comprises ethyl acetate or iso-propyl acetate.

Embodiment 1.25

The method of Embodiment 1.24 wherein the water immiscible solvent comprises ethyl acetate.

Embodiment 1.26

The method described in step (C) of the Summary of the Invention or any one of Embodiments 1.23 through 1.25 wherein the acid of Formula 5 comprises hydrogen chloride, hydrogen bromide, trifluoroacetic acid, sulfuric acid, methane sulfonic acid or phosphoric acid.

Embodiment 1.27

The method of Embodiment 1.26 wherein the acid of Formula 5 comprises hydrogen chloride, hydrogen bromide and sulfuric acid.

Embodiment 1.28

The method of Embodiment 1.27 wherein the acid of Formula 5 comprises hydrogen chloride.

Embodiment 1.29

The method of Embodiment 1.28 wherein the hydrogen chloride is in aqueous solution (i.e. hydrochloric acid).

Embodiment 1.30

The method of Embodiment 1.28 wherein the hydrogen chloride is anhydrous (i.e. hydrogen chloride gas).

Embodiment 1.31

The method described in step (C) of the Summary of the Invention or any one of Embodiments 1.23 through 1.30 wherein the mixture is at a temperature of at least about 20° C.

Embodiment 1.32

The method described in step (C) of the Summary of the Invention or any one of Embodiments 1.23 through 1.31 wherein the mixture is at a temperature of no more than about 45° C.

Embodiment 1.33

The method described in step (C) of the Summary of the Invention or any one of Embodiments 1.23 through 1.32 wherein the molar ratio of the compound of Formula 1 to the acid of Formula 5 is at least about 1.0.

Embodiment 1.34

The method described in step (C) of the Summary of the Invention or any one of Embodiments 1.23 through 1.33 wherein the molar ratio of the compound of Formula 1 to the acid of Formula 5 is no more than about 5.0.

Embodiment 2.0

The method described in step (A1) of the Summary of the Invention wherein the compounds of Formulae 8 and 3 and the coupling reagent are contacted in the presence of a base and a water immiscible solvent.

Embodiment 2.1

The method of Embodiment 2.0 wherein the water immiscible solvent comprises ethyl acetate or iso-propyl acetate.

Embodiment 2.2

The method of Embodiment 2.1 wherein the water immiscible solvent comprises ethyl acetate.

Embodiment 2.3

The method described in step (A1) of the Summary of the Invention or any one of Embodiments 2.0 through 2.2 wherein the compound of Formula 8 is first contacted with the coupling reagent to form a mixture (i.e. containing the acyl imidazole of Formula 9) and then the compound of Formula 3 is added to the mixture.

Embodiment 2.4

The method described in step (A1) of the Summary of the Invention or any one of Embodiments 2.0 through 2.3 wherein the coupling reagent comprises iso-butyl chloroformate or N,N'-carbonyldiimidazole.

Embodiment 2.5

The method of Embodiment 2.4 wherein the coupling reagent comprises N,N'-carbonyldiimidazole.

Embodiment 2.6

The method described in step (A1) of the Summary of the Invention or any one of Embodiments 2.0 through 2.5 wherein the base comprises a basic reagent other than a compound derived from the coupling reagent.

Embodiment 2.7

The method of Embodiment 2.6 wherein the basic reagent comprises triethylamine or N,N-diisopropylethylamine.

Embodiment 2.8

The method of Embodiment 2.7 wherein the basic reagent comprises triethylamine.

Embodiment 2.9

The method described in step (A1) of the Summary of the Invention or any one of Embodiments 2.0 through 2.8 wherein the base is derived from the coupling reagent and the coupling reagent is N,N'-carbonyldiimidazole.

Embodiment 2.10

The method described in step (A1) of the Summary of the Invention or any one of Embodiments 2.0 through 2.9 wherein the compound of Formula 8 is first contacted with the coupling reagent to form a mixture and then the compound of Formula 3 is added to the mixture in the presence of base.

Embodiment 2.11

The method described in step (A1) of the Summary of the Invention or any one of Embodiments 2.0 through 2.10 wherein the mixture is at a temperature of at least about 15° C.

Embodiment 2.12

The method described in step (A1) of the Summary of the Invention or any one of Embodiments 2.0 through 2.11 wherein the mixture is at a temperature of no more than about 40° C.

Embodiment 2.13

The method described in step (A1) of the Summary of the Invention or any one of Embodiments 2.0 through 2.12 wherein the molar ratio of the coupling reagent to the compound of Formula 8 is about 1.0.

Embodiment 2.14

The method described in step (A1) of the Summary of the Invention or any one of Embodiments 2.0 through 2.13 wherein the molar ratio of the compound of Formula 3 to the compound of Formula 8 is about 1.0.

Embodiment 2.15

The method described in step (B1) of the Summary of the Invention wherein the compounds of Formulae 7 and 5 are contacted in the presence of a water immiscible solvent.

Embodiment 2.16

The method of Embodiment 2.15 wherein the water immiscible solvent comprises ethyl acetate or iso-propyl acetate.

Embodiment 2.17

The method of Embodiment 2.16 wherein the water immiscible solvent comprises ethyl acetate.

Embodiment 2.18

The method described in step (B1) of the Summary of the Invention or any one of Embodiments 2.15 through 2.17 wherein the acid of Formula 5 comprises hydrogen chloride, hydrogen bromide, trifluoroacetic acid, sulfuric acid, methane sulfonic acid or phosphoric acid.

Embodiment 2.19

The method of Embodiment 2.18 wherein the acid of Formula 5 comprises hydrogen chloride, hydrogen bromide and sulfuric acid.

Embodiment 2.20

The method of Embodiment 2.19 wherein the acid of Formula 5 comprises hydrogen chloride.

Embodiment 2.21

The method of Embodiment 2.20 wherein the hydrogen chloride is in aqueous solution (i.e. hydrochloric acid).

Embodiment 2.22

The method of Embodiment 2.20 wherein the hydrogen chloride is anhydrous (i.e. hydrogen chloride gas).

Embodiment 2.23

The method described in step (B1) of the Summary of the Invention or any one of Embodiments 2.15 through 2.22 wherein the mixture is at a temperature of at least about 20° C.

Embodiment 2.24

The method described in step (B1) of the Summary of the Invention or any one of Embodiments 2.15 through 2.23 wherein the mixture is at a temperature of no more than about 45° C.

Embodiment 2.25

The method described in step (B1) of the Summary of the Invention or any one of Embodiments 2.15 through 2.24 wherein the molar ratio of the compound of Formula 7 to the acid of Formula 5 is at least about 1.0.

Embodiment 2.26

The method described in step (B1) of the Summary of the Invention or any one of Embodiments 2.15 through 2.25 wherein the molar ratio of the compound of Formula 7 to the acid of Formula 5 is no more than about 5.0.

Embodiment 3.0

The method described in the Summary of the Invention for preparing the compound of Formula 14 wherein the compounds of Formulae 1 or 1A and Formula 15 and the coupling reagent are contacted in the presence of a base and a polar aprotic water miscible solvent.

Embodiment 3.1

The method of Embodiment 3.0 wherein the polar aprotic water miscible solvent comprises acetonitrile, tetrahydrofuran or dioxane.

Embodiment 3.2

The method of Embodiment 3.1 wherein the polar aprotic water miscible solvent comprises acetonitrile.

Embodiment 3.3

The method described in the Summary of the Invention for preparing the compound of Formula 14 or any one of Embodiments 3.0 through 3.2 wherein the coupling reagent comprises iso-butyl chloroformate or N,N'-carbonyldiimidazole.

Embodiment 3.4

The method of Embodiment 3.3 wherein the coupling reagent comprises N,N'-carbonyldiimidazole.

Embodiment 3.5

The method described in the Summary of the Invention for preparing the compound of Formula 14 or any one of Embodiments 3.0 through 3.4 wherein the base comprises a basic reagent other than a compound derived from the coupling reagent.

Embodiment 3.6

The method of Embodiment 3.5 wherein the basic reagent comprises triethylamine or N,N-diisopropylethylamine.

Embodiment 3.7

The method of Embodiment 3.6 wherein the basic reagent comprises triethylamine.

Embodiment 3.8

The method described in the Summary of the Invention for preparing the compound of Formula 14 or any one of Embodiments 3.0 through 3.7 wherein the base is derived from the coupling reagent and the coupling reagent is N,N'-carbonyldiimidazole.

Embodiment 3.9

The method described in the Summary of the Invention for preparing the compound of Formula 14 or any one of Embodiments 3.0 through 3.8 wherein the compound of Formula 15 is first contacted with the coupling reagent to form a mixture (i.e. containing the acyl imidazole of Formula 16) and then the compound of Formula 1 or 1A is added to the mixture in the presence of base.

Embodiment 3.10

The method described in the Summary of the Invention for preparing the compound of Formula 14 or any one of Embodiments 3.0 through 3.9 wherein the compound of Formula 1 or 1A is added to the mixture as a solid or a solution in the polar aprotic water miscible solvent.

Embodiment 3.11

The method described in the Summary of the Invention for preparing the compound of Formula 14 or any one of Embodiments 3.0 through 3.10 wherein the compound of Formula 1 or 1A is added to the mixture as a solution or slurry in water.

Embodiment 3.12

The method described in the Summary of the Invention for preparing the compound of Formula 14 or any one of Embodiments 3.0 through 3.12 wherein the mixture is at a temperature of at least about 20° C.

Embodiment 3.13

The method described in the Summary of the Invention for preparing the compound of Formula 14 or any one of Embodiments 3.0 through 3.12 wherein the mixture is at a temperature of no more than about 45° C.

Embodiment 3.14

The method described in the Summary of the Invention for preparing the compound of Formula 14 or any one of Embodiments 3.0 through 3.13 wherein the molar ratio of the coupling reagent to the compound of Formula 15 is about 1.0 to about 1.1.

Embodiment 3.15

The method described in the Summary of the Invention for preparing the compound of Formula 14 or any one of Embodiments 3.0 through 3.14 wherein the molar ratio of the compound of Formula 1 or 1A to the compound of Formula 15 is about 1.0.

Embodiments of this invention, including Embodiments 1.0-3.15 above as well as any other embodiments described herein, can be combined in any manner, and the descriptions of variables in the embodiments pertain not only to the aforedescribed methods for preparing compounds of Formulae 1, 1A and 14 but also to the starting compounds and intermediate compounds useful for preparing the compounds of Formulae 1, 1A and 14 by these methods.

In the following Schemes 1-9 the definition of X in the compounds of Formulae 1 through 16 are as defined above in the Summary of the Invention and description of Embodiments unless otherwise indicated.

In the method of the invention, a benzyl carbamate (CBZ) amine protecting group is used in the preparation of a compound of Formula 1 as shown in Schemes 1 and 2. The compound of Formula 1 can be further reacted with acid to form the acid salt of Formula 1A as shown in Scheme 3 (see synthesis Examples 1 and 2).

Step B of the method of the invention involves removal of the benzyl carbamate protecting group in an intermediate of Formula 4 via hydrogenolysis to give the free amine compound of Formula 1 as shown in Scheme 1.

Scheme 1

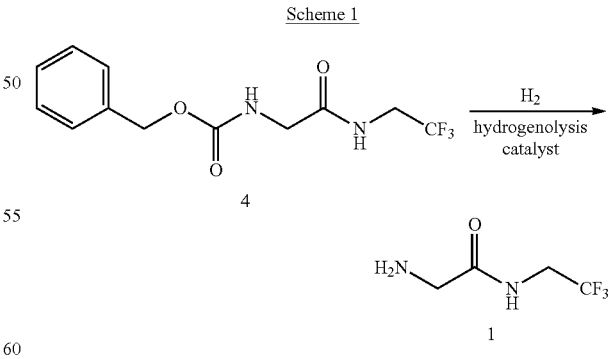

Removal of benzyl carbamate protecting groups can be accomplished with a variety of reaction conditions. See, for example, Greene, T. W.; Wuts, P. G. M. *Protective Groups in Organic Synthesis,* 2nd ed.; Wiley: New York, 1991. One particularly useful method for removal of the benzyl protecting group is via hydrogenolysis with hydrogen, usually under atmospheric pressure. Precious metal catalysts or supported precious metal catalysts are commonly used. Hydrogenolysis can also be accomplished by hydrogen transfer with a supported precious metal catalyst and a hydrogen donor (i e ammonium formate or cyclohexadiene). These methods are described in Rylander, P. N.; *Hydrogenation Methods*, Academic Press: San Diego, 1985. One particularly useful catalyst for the hydrogenolysis is palladium on carbon (usually 5-10%). This method is described in Harada et al., *Bioorganic and Medicinal Chemistry* 2001, 9, 2709-2726 and Janda et al., *Synthetic Communications* 1990, 20, 1073-1082. The benzyl carbamate protecting group can also be removed with acid as described in Lesk et al., *Synthetic Communications* 1999, 28, 1405-1408.

The method of Scheme 1 can be conducted over a range of temperatures. Typically the reaction temperature is at least about 20° C. or ambient temperature. The hydrogenation can be conducted over a range of pressures. Typically the hydrogenation is conducted at atmospheric pressure using a hydrogen balloon. The time needed for reaction is usually between 2 and 24 hours depending on the scale of the reaction.

In the present method the reaction mixture comprises a water immiscible solvent. Solvents that have been found to be particularly useful are ethyl acetate and iso-propyl acetate. Polar aprotic solvents that are water immiscible are particularly useful because of their ability to dissolve the starting material of Formula 4. The amount of solvent used is the volume needed to dissolve the starting material, usually in the range of 0.5 to 1.0 molar concentration. The mixture of the starting material and solvent can be warmed to about 30° C. to aid the dissolution of the compound of Formula 4 and enable the concentration of the reaction mixture to be greater than 0.5 molar.

Reaction progress can be monitored by conventional methods such as thin layer chromatography, GC, HPLC and $^1$H NMR analyses of aliquots. After completion of the reaction, the product is separated from the catalyst by filtration. The resultant solution contains the free amine compound of Formula 1. This solution can be concentrated to isolate the compound of Formula 1. Alternatively the solution can be further reacted with acid as in Scheme 3 to make the compound of Formula 1A. Another alternative is adding water to the filtered solution wherein the compound of Formula 1 will partition into the water and form an aqueous solution which can be separated and used in subsequent reactions.

Step A of the method of the invention is the reaction of benzyl carbamate protected starting material of Formula 2 with a compound of Formula 3 to give the intermediate of Formula 4 is shown in Scheme 2. Step A involves first activation of the carboxylic acid functional group of the compound of Formula 2 with the coupling reagent to form an acyl imidazole compound of Formula 6. The acyl imidazole intermediate of Formula 6 can be isolated, but most of time it is not isolated and instead is treated directly with the amine of Formula 3 to form an amide bond to give the compound of Formula 4.

Scheme 2

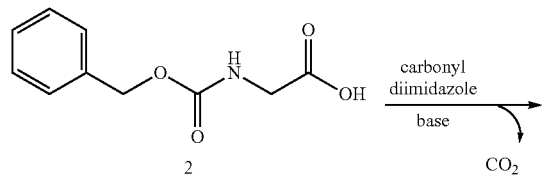

A variety of coupling reagents can be used in to prepare the compound of Formula 4. Several alkyl chloroformates and carbonyl diheteroaryl reagents have been discovered to be particularly efficacious in providing high yields of compounds of Formula 6. These coupling reagents include methyl chloroformate, ethyl chloroformate, iso-butyl chloroformate N,N'-carbonyldiimidazole and 1,1'-carbonylbis (3-methylimidazolium)triflate, with N,N'-carbonyldiimidazole (also referred to as carbonyldiimidazole) preferred. N,N'-carbonyldiimidazole (shown in Scheme 2) is the most efficient coupling reagent because it provides one equivalent of base to neutralize the amine salt of Formula 3. Chloroformate ester coupling reagents require the addition of a basic reagent to neutralize the acid generated from the reaction with a compound of Formula 2 and to liberate the free base of the compound of Formula 3. An especially useful base for this reaction is triethylamine.

The stoichiometry of this reaction involves equimolar amounts of the compound of Formula 2 and the coupling reagent and the base. When N,N'-carbonyldiimidazole is the coupling reagent, one equivalent of carbon dioxide is evolved during formation of the acyl imidazole intermediate (compound of Formula 6). An equivalent of imidazole is also released during formation of the acyl imidazole and it reacts with one equivalent of hydrogen chloride when the amine salt of Formula 3 is added to the reaction mixture. Therefore, the base can be derived from the coupling reagent when the coupling reagent is N,N'-carbonyldiimidazole. An equivalent of additional base (basic reagent not derived from the coupling reagent) like triethylamine is optional when N,N'-carbonyldiimidazole is the coupling reagent. Additional base (for example triethylamine or diisopropylethylamine) will speed the reaction since it is more basic than imidazole and reacts faster with the hydrogen chloride salt of Formula 3 to release its free base form for reaction with the acyl imidazole. The molar ratio of the coupling reagent to the compound of Formula 2 can range from about 0.95 to about 1.15 however a ratio of at least 1.0 is preferred to ensure complete formation of the acyl imidazole intermediate of Formula 6.

The stoichiometry of the reaction further involves equimolar amounts of the compound of Formula 3 and the compound of Formula 2. The molar ratio of the compound of Formula 3 to the compound of Formula 2 can range from about 1.0 to about 1.15 however a ratio of at least 1.05 is preferred to ensure complete reaction of the acyl imidazole intermediate with the compound of Formula 3.

The order of addition of the reactants in step A of the method of the invention is very important. The compound of Formula 2 can be dissolved in the solvent and the coupling reagent added to it or the coupling reagent can be dissolved in the solvent and the compound of Formula 2 added to it. However, it is important to give the acyl imidazole formation enough time before the addition of the compound of Formula 3. The acyl imidazole formation can usually be monitored by evolution of carbon dioxide gas over 1 to 2 hours depending on the scale of the reaction.

The compounds of Formula 2 and Formula 3 are commercially available. The compound of Formula 3 is particularly preferred because of its ease in handling. Trifluoroethyl amine can be used in its neutral state but it is volatile (boiling point 36-37° C.) and less convenient.

In the present method the reaction mixture comprises a water immiscible solvent. Solvents that have been found to be particularly useful are ethyl acetate and iso-propyl acetate. Polar aprotic solvents that are water immiscible are particularly useful because of their ability to dissolve the starting material of Formula 2 and can be separated from water in an aqueous workup. The amount of solvent used is the volume needed to dissolve the starting material, usually in the range of 0.75 to 1.5 molar concentration with 1.0 molar concentration being particularly useful.

The reaction of the method of Scheme 2 can be conducted over a wide range of temperatures. Typically the reaction temperature is at least about 15° C. and most typically at least about 20° C. Typically the reaction temperature is no more than about 40° C. and most typically no more than about 35° C.

Reaction progress can be monitored by conventional methods such as thin layer chromatography, GC, HPLC and $^1$H NMR analyses of aliquots. After completion of the reaction, the mixture is typically worked up by addition of an aqueous mineral acid such as hydrochloric acid. Separation of the organic phase, further washing with hydrochloric acid (1.0 N) to remove imidazole (and any optional triethylamine that was added), drying over desiccants such as magnesium sulfate or molecular sieves, or azeotropic drying and then evaporation of the solvent leaves the product of Formula 4, as a colorless solid. Evaporation of the solvent is optional; when azeotropic drying is employed the solvent is not removed and a solution of a compound of Formula 4 is carried forward.

Step C of the method of the invention is optional and involves the reaction of the free amine of Formula 1 with an acid of Formula 5 to give the acid salt of Formula 1A as shown in Scheme 3.

Scheme 3

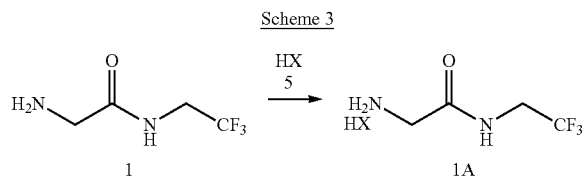

wherein X is Cl, Br, $CF_3CO_2$, $CH_3SO_3$, $(SO_4)_{1/2}$ or $(PO_4)_{1/3}$.

The free amine of Formula 1 is sensitive to air. The resultant solution (from step B) of the compound of Formula 1 can be treated with acid to produce the more stable acid salt of Formula 1A. The compound of Formula 1A is then isolated by filtration and dried in a vacuum oven (50-60° C.) or air dried. The salt of Formula 1A can be stored at ambient conditions without the deleterious effects from weight gain from moisture and air exposure and handling problems from a hygroscopic sticky texture. See Example 12 for comparison of the compounds of Formula 1 and 1A and other salts.

Non-aqueous acids of Formula 5 have been discovered to be particularly efficacious in providing high yields of compounds of Formula 1A. These acids include hydrogen chloride, hydrogen bromide, trifluoroacetic acid, methane sulfonic acid, sulfuric acid or phosphoric acid with hydrogen chloride preferred for its low cost. The acid is usually bubbled into the catalyst free reaction mixture or in the case of liquid acids added dropwise. The non-aqueous acids of Formula 5 are added to the water immiscible solvent solution from step B to give the solid salt of Formula 1A that can be easily isolated by filtration. Alternatively aqueous acids of Formula 5 (for example concentrated hydrochloric acid) can be added dropwise to the solution of Formula 1 from step B to give an aqueous phase containing the compound of Formula 1A. This aqueous phase can be separated from the water immiscible solvent and used in subsequent reactions.

An alternative to the benzyl carbamate (CBZ) amine protecting group used in the method of the invention in Schemes 1 and 2 is the tert-butyl carbamate (BOC) amine protecting group shown in Schemes 4 and 5 (see synthesis Examples 3 and 4).

In step B of the method of the invention illustrated in Scheme 4, a compound of Formula 1A is directly prepared by contacting a compound of Formula 7 with an acid of Formula 5. The reaction involves both removal of a tert-butyl carbamate protecting group and simultaneous formation of the salt of an amine functional group.

Scheme 4

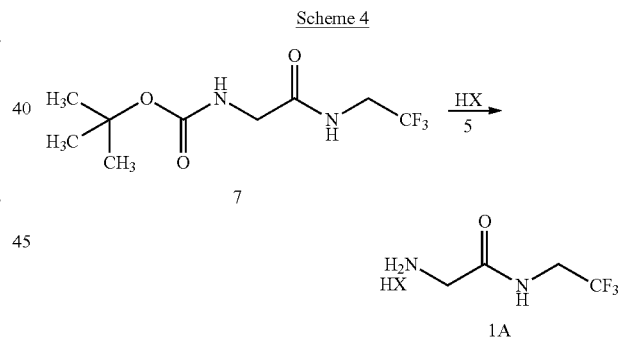

wherein X is Cl, Br, $CF_3CO_2$, $CH_3SO_3$, $(SO_4)_{1/2}$ or $(PO_4)_{1/3}$.

The stoichiometry of this reaction involves equimolar amounts of the acid of Formula 5 relative to the compound of Formula 7. However, a molar excess of about 2.0 to about 5.0 of the acid of Formula 5 is desirable to ensure complete removal of the tert-butyl carbamate protecting group from the compound of Formula 7 and complete formation of the acid salt of Formula 1A.

Non-aqueous acids of Formula 5 have been discovered to be particularly efficacious in providing high yields of compounds of Formula 1A. These acids include hydrogen chloride, hydrogen bromide, trifluoroacetic acid, methane sulfonic acid, sulfuric acid or phosphoric acid with hydrogen chloride preferred for its low cost. The anhydrous acids in the form of a gas like hydrogen chloride (see synthesis Example 4 step B) are usually bubbled into the reaction mixture. In the case of liquid acids like trifluoroacetic acid (see synthesis Example 7) the liquid is added dropwise. The non-aqueous acids of Formula 5 are used in a water immiscible solvent to give a solid salt of Formula 1A that can be easily isolated by filtration of the reaction mixture. Formation and isolation of the product salt using the above procedure avoids an aqueous workup step. The isolated solid salt of Formula 1A can be used in subsequent reactions.

Aqueous acids of Formula 5 have been discovered to also be efficacious in providing high yields of compounds of Formula 1A. These acids include hydrochloric acid and hydrobromic acid with hydrochloric acid preferred for its low cost (see synthesis Example 4 Step B1). The aqueous acid is usually dripped into the reaction mixture. When the aqueous acids of Formula 5 are used in a water immiscible solvent, the salt of Formula 1A is formed and then dissolved in a water phase that separates from the organic phase. The concentrated aqueous solution of the compound of Formula 1A can be easily isolated by drawing off the more dense aqueous phase from the bottom of the reaction vessel. The concentrated aqueous solution of the compound of Formula 1A can be used in subsequent reactions.

In the present method the reaction mixture comprises a water immiscible solvent. Solvents that have been found to be particularly useful are ethyl acetate and iso-propyl acetate. Polar aprotic solvents that are water immiscible are particularly useful because of their ability to dissolve the starting material of Formula 7 and cause the precipitation of the product of Formula 1A. The amount of solvent used is the volume needed to dissolve the starting material, usually in the range of 0.5 to 1.0 molar concentration. The mixture of the starting material and solvent can be warmed to about 30° C. to aid the dissolution of the compound of Formula 7 and enable the concentration of the reaction mixture to be greater than 0.5 molar. Once the starting material is dissolved the heating source is removed and the acid is added to the reaction mixture at ambient temperature.

The method shown in Scheme 4 can be conducted over a wide range of temperatures. Typically the reaction temperature is at least about 20° C. or ambient temperature. The reaction mixture usually warms during the reaction but the exotherm usually does not require external cooling and reaction temperature usually remains below the boiling point of the solvent. Typically the reaction temperature is no more than about 45° C. and most typically no more than about 40° C.

Reaction progress can be monitored by conventional methods such as thin layer chromatography, GC, HPLC and $^1$H NMR analyses of aliquots. After completion of the reaction, the mixture is typically cooled to room temperature and the product isolated by conventional methods, such as filtration. The solid product recovered by filtration can be dried in a vacuum oven (50-60° C.) or air dried.

In step A of the method of the invention illustrated in Scheme 5, a compound of Formula 7 is prepared by contacting a compound of Formula 8 with a compound of Formula 3 and a coupling reagent. The method to prepare a compound of Formula 7 involves first activation of the carboxylic acid functional group of the compound of Formula 8 with the coupling reagent to form an acyl imidazole compound of Formula 9. The acyl imidazole compound of Formula 9 can be isolated, but is usually not isolated. It forms an amide bond with the amine functional group in the compound of Formula 3 to give the compound of Formula 7.

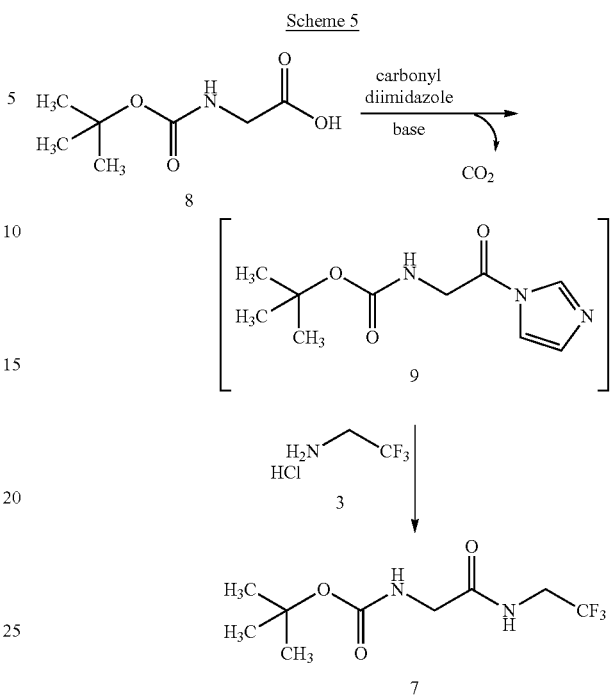

Scheme 5

The stoichiometry of this reaction involves equimolar amounts of the compound of Formula 8 and the coupling reagent and the base. When N,N'-carbonyldiimidazole is the coupling reagent, one equivalent of carbon dioxide is evolved during formation of the acyl imidazole intermediate (compound of Formula 9). An equivalent of imidazole is also released during formation of the acyl imidazole and it reacts with one equivalent of hydrogen chloride when the amine salt of Formula 3 is added to the reaction mixture. Therefore, the base can be derived from the coupling reagent when the coupling reagent is N,N'-carbonyldiimidazole. An equivalent of additional base (basic reagent not derived from the coupling reagent) like triethylamine is optional when N,N'-carbonyldiimidazole is the coupling reagent. Additional base (for example triethylamine or diisopropylethylamine) will speed the reaction since it is more basic than imidazole and reacts faster with the hydrogen chloride salt of Formula 3 to release its free base form for reaction with the acyl imidazole. The molar ratio of the coupling reagent to the compound of Formula 2 can range from about 0.95 to about 1.15 however a ratio of at least 1.0 is preferred to ensure complete formation of the acyl imidazole intermediate of Formula 9. The stoichiometry of the reaction involves equimolar amounts of the compound of Formula 3 and the compound of Formula 8. The molar ratio of the compound of Formula 3 to the compound of Formula 8 can range from about 1.0 to about 1.15 however a ratio of at least 1.05 is preferred to ensure complete reaction of the acyl imidazole intermediate with the compound of Formula 3.

A variety of coupling reagents can be used for step A. Several alkyl chloroformates and carbonyl diheteroaryl reagents have been discovered to be particularly efficacious in providing high yields of compounds of Formula 7. These coupling reagents include methyl chloroformate, ethyl chloroformate, iso-butyl chloroformate N,N'-carbonyldiimidazole and 1,1'-carbonylbis(3-methylimidazolium)triflate, with N,N'-carbonyldiimidazole (also referred to as carbonyldiimidazole) preferred. N,N'-carbonyldiimidazole is the most efficient coupling reagent because it provides one equivalent of base to neutralize the amine salt of Formula 3. Chloroformate ester coupling reagents require the addition of a basic reagent to neutralize the acid generated from the reaction with a compound of Formula 8 and to liberate the free base of the compound of Formula 3 (see synthesis Example 6). An especially useful base for this reaction is triethylamine.

The order of addition of the reactants in step A of the method of the invention is very important. The compound of Formula 8 can be dissolved in the solvent and the coupling reagent added to it or the coupling reagent can be dissolved in the solvent and the compound of Formula 8 added to it. However, it is important to give the acyl imidazole intermediate formation enough time before the addition of the compound of Formula 3. The acyl imidazole intermediate formation can usually be monitored by evolution of carbon dioxide gas over 1 to 2 hours depending on the scale of the reaction.

The compounds of Formula 8 and Formula 3 are commercially available. The compound of Formula 3 is particularly preferred because of its ease in handling. Trifluoroethyl amine can be used in its neutral state but it is volatile (boiling point 36-37° C.) and less convenient. A compound of Formula 7 can also be prepared from commercially available N—BOC-glycine N-carboxyanhydride (see synthesis Example 5).

In the present method the reaction mixture comprises a water immiscible solvent. Solvents that have been found to be particularly useful are ethyl acetate and iso-propyl acetate. Polar aprotic solvents that are water immiscible are particularly useful because of their ability to dissolve the starting material of Formula 8 and can be separated from water in an aqueous workup. The amount of solvent used is the volume needed to dissolve the starting material, usually in the range of 0.75 to 1.5 molar concentration with 1.0 molar concentration being particularly useful.

The reaction of the method of Scheme 5 can be conducted over a wide range of temperatures. Typically the reaction temperature is at least about 15° C. and most typically at least about 20° C. The reaction mixture usually warms during the reaction but the exotherm usually does not require external cooling and reaction temperature usually remains below the boiling point of the solvent. Typically the reaction temperature is no more than about 40° C. and most typically no more than about 35° C.

Reaction progress can be monitored by conventional methods such as thin layer chromatography, GC, HPLC and $^1$H NMR analyses of aliquots. After completion of the reaction, the mixture is typically worked up by addition of a dilute aqueous mineral acid such as hydrochloric acid. Separation of the organic phase, further washing with hydrochloric acid (1.0 N) to remove imidazole or other added base, drying over desiccants such as magnesium sulfate or molecular sieves, or azeotropic drying and then evaporation of the solvent leaves the compound of Formula 7, as a colorless solid. Evaporation of the solvent is optional; when azeotropic drying is employed the solvent is not removed and a solution of a compound of Formula 7 is carried forward.

Another alternative to the benzyl carbamate (CBZ) amine protecting group used in the method of the invention in Schemes 1 and 2 is the dibenzyl amine protecting group shown in Schemes 6, 7 and 8 (see synthesis Example 8).

The dibenzyl amine alternative process involves removal of a dibenzyl protecting group in an intermediate of Formula 10 via hydrogenolysis to give the free amine compound of Formula 1 as shown in Scheme 6.

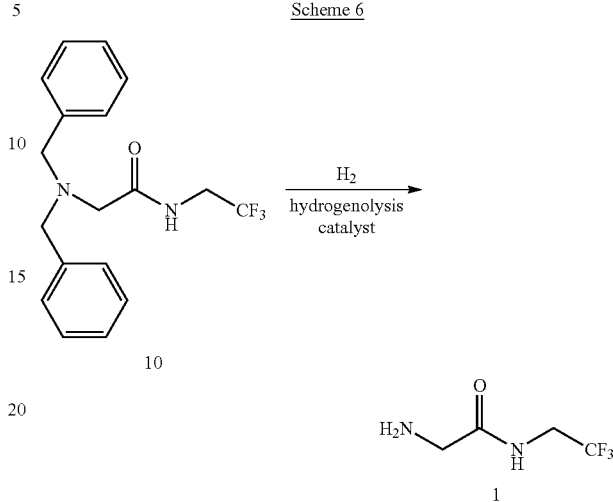

Removal of the benzyl protecting groups can be accomplished with a variety of reaction conditions. See, for example, Greene, T. W.; Wuts, P. G. M. *Protective Groups in Organic Synthesis,* 2nd ed.; Wiley: New York, 1991. One particularly useful method for removal of the benzyl protecting group on nitrogen is via hydrogenolysis with hydrogen using precious metal catalysts, usually under pressure. This method is described in Rylander, P. N.; *Hydrogenation Methods,* Academic Press: San Diego, 1985. One particularly useful catalyst for the hydrogenolysis is palladium on carbon (5-10%).

Removal of benzyl protecting groups from nitrogen requires more vigorous conditions than removal of the benzyl protecting group from oxygen (as in the BOC procedure). The hydrogenolysis reaction is usually conducted under pressure and at elevated temperature. A pressure of 50-100 psi of hydrogen is typical. Typically the reaction temperature is 50 to 80° C. Temperatures in the range of about 70° C. are preferred. The reaction is not exothermic and requires external heating to maintain the desired temperature In the method of Scheme 6, the reaction mixture comprises an organic solvent. Solvents that have been found to be particularly useful are methanol and ethanol, other solvents typically used for hydrogenation can also be used. The amount of organic solvent used is the volume needed to dissolve the starting material, usually in the range of 0.3 to 1.0 molar concentration. The mixture of the starting material of Formula 10 in the solvent is heated to the desired temperature under hydrogen pressure. The reaction is heated until the reaction is complete, as indicated by the cease of hydrogen uptake.

Reaction progress can be monitored by conventional methods such as thin layer chromatography, GC, HPLC and $^1$H NMR analyses of aliquots, or by rate of hydrogen uptake. After completion of the reaction, the mixture is typically cooled to ambient temperature and filtered to remove the supported catalyst. The product compound of Formula 1 is isolated by concentration and is recovered as an oil.

The compound of Formula 10 can be prepared by contacting a compound of Formula 11 with a compound of Formula 12 in the presence of a base. The alkylation of the amine of Formula 12 with the alkyl chloride of Formula 11 is shown in Scheme 7.

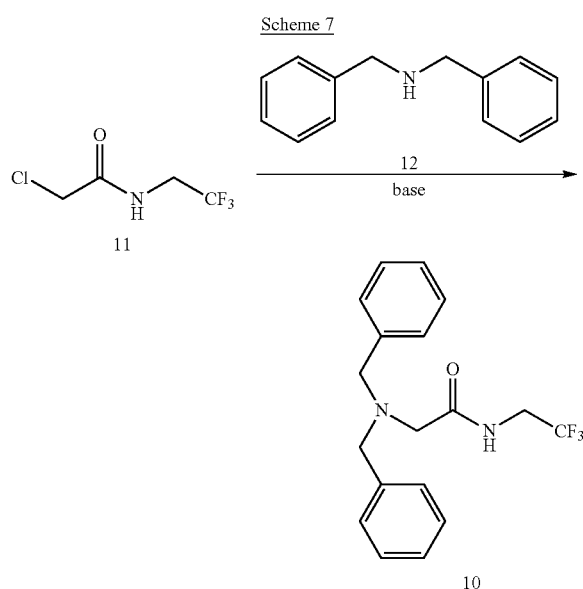

The stoichiometry of this reaction involves equimolar amounts of the chloroacetyl amide of Formula 11 relative to the amine of Formula 12. However, a molar excess of about 1.1 to about 1.2 of the amine of Formula 12 is desirable to ensure complete reaction of the chloroacetamide of Formula 11 and complete formation of the dibenzyl amine of Formula 10. The reaction also requires an equimolar amount of base. Depending on the base used, a molar excess of up to 2.0 equivalents may be required. The preferred base is a tertiary amine, such as triethylamine or Hunig's base (diisoproply-ethylamine), but alkali metal carbonates can be used.

In the method shown in Scheme 7 the reaction mixture comprises an organic solvent. A solvent that has been found to be particularly useful is methanol, but aromatic solvents, such as toluene, or polar aprotic solvents, such as acetonitrile, can also be used. The amount of organic solvent used is the volume needed to dissolve the starting materials, usually in the range of 0.5 to 1.0 molar concentration with 0.7 molar concentration being particularly useful. The mixture of the starting chloroacetyl amide, dibenzylamine and base in the solvent are heated to reflux, or to higher temperatures by running under pressure. Temperatures in the range of 80 to 100° C. are preferred. The reaction is heated until the reaction is complete, typically 12 to 24 hours.

Reaction progress can be monitored by conventional methods such as thin layer chromatography, GC, HPLC and $^1$H NMR analyses of aliquots. After completion of the reaction, the mixture is typically cooled to ambient temperature and concentrated to remove the solvent. The oil residue is dissolved in methylene chloride, or similar solvent, and washed at least twice with water. The product is isolated by conventional methods, such as concentration. The oil product recovered by concentration crystallizes on cooling.

The starting material dibenzylamine (a compound of Formula 12) is commercially available.

The compound of Formula 11 can be prepared by contacting a compound of Formula 13 with a compound of Formula 3A in the presence of a base. The reaction of the amine of Formula 3A with the acid chloride of Formula 13 is shown in Scheme 8.

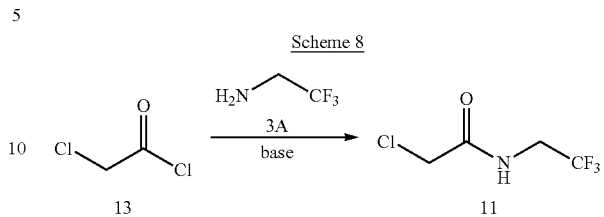

The stoichiometry of this reaction involves equimolar amounts of the acid chloride of Formula 13 relative to the amine of Formula 3A. However, a molar excess of about 1.05 to about 1.1 of the acid chloride of Formula 13 is desirable to ensure complete reaction of the amine of Formula 3A and complete formation of the product of Formula 11. The reaction also requires and equimolar amount of base. A molar excess similar to the molar excess of acid chloride is advantageous. The preferred base is potassium carbonate, but a variety of alkali metal carbonates or bicarbonates can be used.

In the method of Scheme 8 the reaction mixture comprises a two phase system of water and a water immiscible solvent. Solvents that have been found to be particularly useful are ethyl acetate and diethyl ether. The amount of organic solvent used is the volume needed to dissolve the starting materials, usually in the range of 1.0 to 1.5 molar concentration for the amine and 4.0 to 5.0 molar for the acid chloride. The amount of water used is the volume needed to dissolve the alkali metal carbonate base and varies according to the solubility of the based used. With potassium carbonate a concentration range of 1.0 to 3.0 molar concentration is typical. The mixture of the starting trifluoroethyl amine (compound of Formula 3A) in solvent and the carbonate in water is agitated and cooled to about −5 to 0° C. The solution of the chloroacetyl chloride (compound of Formula 13) in the solvent is added to the cooled reaction mixture over 0.5 to 2 hours while maintaining the temperature at −5 to 0° C., then the reaction is stirred at that temperature for 1 hour.

The reaction of the method of Scheme 8 can be conducted over a narrow range of temperatures. Typically the reaction temperature is below 10° C. and most typically below 0° C. The reaction is exothermic and requires external cooling to maintain the desired temperature.

Reaction progress can be monitored by conventional methods such as thin layer chromatography, GC and $^1$H NMR analyses of aliquots. After completion of the reaction, the mixture is typically phase separated and the solvent phase washed with water, and the product isolated by concentration of the solvent. The oil product recovered by concentration crystallizes on standing.

The starting materials chloroacetyl chloride (compound of Formula 13) and trifluoroethyl amine (compound of Formula 3A) are commercially available.

In another aspect of the present invention, compounds of Formula 14 are prepared from compounds of Formula 1 or Formula 1A. In the method shown in Scheme 9, a compound of Formula 15 is contacted with a coupling reagent to form an intermediate of Formula 16. The acyl imidazole intermediate of Formula 16 can be isolated (see synthesis Example 9). Most of time the acyl imidazole is not isolated and instead is treated directly with a compound of Formula 1 or 1A to form the compound of Formula 14.

Scheme 9

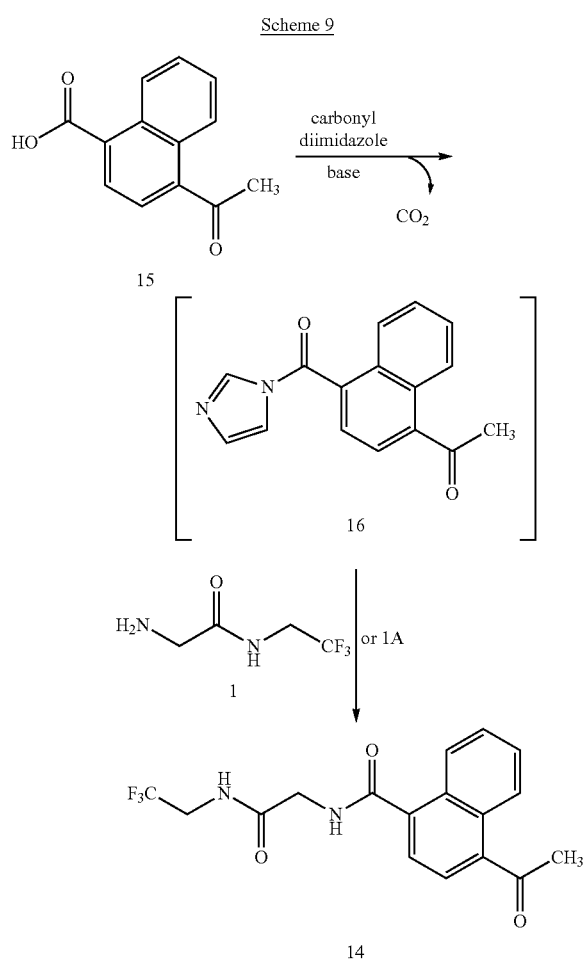

When N,N'-carbonyldiimidazole is the coupling reagent, one equivalent of carbon dioxide is evolved during formation of the acyl imidazole intermediate (compound of Formula 16). An equivalent of imidazole is also released during formation of the acyl imidazole and it reacts with one equivalent of acid (i.e. hydrogen chloride, hydrogen bromide, trifluoroacetic acid, methane sulfonic acid, sulfuric acid or phosphoric acid) when the amine salt of Formula 1A is added to the reaction mixture. Therefore, the base can be derived from the coupling reagent when the coupling reagent is N,N'-carbonyldiimidazole. An equivalent of additional base (basic reagent not derived from the coupling reagent) like triethylamine is optional when N,N'-carbonyldiimidazole is the coupling reagent. Additional base (for example triethylamine or diisopropylethylamine) will speed the reaction since it is more basic than imidazole and reacts faster with the hydrogen chloride salt of Formula 1A to release its free base form for reaction with the acyl imidazole. Alternatively the acyl imidazole of Formula 16 can be reacted with the free amine of Formula 1 instead of its acid salt of Formula 1A. No additional base is needed when the free amine of Formula 1 is used in the preparation of the compound of Formula 14. See synthesis Example 10 for reaction using a compound of Formula 1 and synthesis Example 11 for reaction using a compound of Formula 1A.

The stoichiometry of the reaction in Scheme 9 involves equimolar amounts of the compound of Formula 15 and the coupling reagent and the base. The molar ratio of the coupling reagent to the compound of Formula 15 can range from about 0.95 to about 1.15 however a ratio of about 0.97 is preferred to maximize formation of the acyl imidazole intermediate of Formula 16 without any excess N,N'-carbonyldiimidazole left over. The stoichiometry of the reaction involves equimolar amounts of the compound of Formula 1 or 1A and the compound of Formula 15. The molar ratio of the compound of Formula 1 or 1A to the compound of Formula 15 can range from about 1.0 to about 1.15 however a ratio of at least 1.05 is preferred to ensure complete reaction of the acyl imidazole intermediate (compound of Formula 16) with the compound of Formula 1 or 1A.

A variety of coupling reagents can be used in Scheme 9. Several alkyl chloroformates and carbonyl diheteroaryl reagents have been discovered to be particularly efficacious in providing high yields of compounds of Formula 14. These coupling reagents include methyl chloroformate, ethyl chloroformate, iso-butyl chloroformate N,N'-carbonyldiimidazole and 1,1'-carbonylbis(3-methylimidazolium)triflate, with N,N'-carbonyldiimidazole (also referred to as carbonyldiimidazole) preferred. N,N'-carbonyldiimidazole is the most efficient coupling reagent because it provides one equivalent of base to neutralize the amine salt of Formula 1A. Chloroformate ester coupling reagents require the addition of a basic reagent to neutralize the acid generated from the reaction with a compound of Formula 15 and to liberate the free base of the compound of Formula 3. An especially useful base for this reaction is triethylamine.

The order of addition of the reactants is important. The coupling reagent is usually dissolved in the solvent and the compound of Formula 15 added to it. It is important to give the acyl imidazole formation enough time before the addition of the compound of Formula 1 or 1A. The acyl imidazole intermediate formation (compound of Formula 16) can usually be monitored by evolution of carbon dioxide gas over 0.5 to 2 hours depending on the scale of the reaction.

The compound of Formula 1 or 1A is commercially available or is prepared by the method of the invention shown in previous Schemes. The compound of Formula 1 or 1A can be added to the mixture as a solid or slurry in a polar aprotic water miscible solvent. The compound of Formula 15 was prepared according to the procedure of F. Feist in *Justus Liebigs Annalen der Chemie* 1932, 496, 99-122. The compound of Formula 1A is especially useful because of its ease in handling since it is not hygroscopic (see Example 16). Use of the neutral free amine compound of Formula 1 is less convenient because it is hygroscopic and exposure to air needs to minimized.

In the present method the reaction mixture comprises a water miscible polar aprotic solvent. Solvents that have been found to be useful are acetonitrile, tetrahydrofuran and dioxane. Acetonitrile was found to be particularly useful. The amount of solvent used is the volume needed to dissolve the starting material, usually in the range of 0.75 to 1.5 molar concentration with 1.0 molar concentration being particularly useful.

The method of Scheme 9 can be conducted over a wide range of temperatures. Typically the reaction temperature is at least about 20° C. and most typically at least about 30° C. The reaction mixture usually warms during the reaction but the exotherm usually does not require external cooling and reaction temperature usually remains below the boiling point of the solvent. Typically the reaction temperature is no more than about 45° C. and most typically no more than about 35° C.

Reaction progress can be monitored by conventional methods such as thin layer chromatography, GC, HPLC and $^1$H NMR analyses of aliquots. After completion of the reaction, the mixture is typically worked up by addition of an aqueous mineral acid such as hydrochloric acid (1.1 mole of 1N). The brief acid treatment is used to hydrolyze any imine that might be formed between the acetyl group on the product (compound of Formula 14) and excess amine from the compound of Formula 1. Then, the pH is adjusted to 9-10 with base (sodium hydroxide or sodium carbonate) resulting in a slurry. The slurry is cooled to 20° C. and filtered. The resultant solid product is washed with water and dried in a vacuum oven (50-60° C.).

An alternative procedure for the preparation of a compound of Formula 14 uses an aqueous solution of a compound of Formula 1 or 1A. Remarkably water can be tolerated in the reaction mixture with the acyl imidazole intermediate of Formula 16. The acyl imidazole intermediate of Formula 16 reacts faster with the more nucleophilic amine of Formula 1 (either added directly or formed by neutralization of the hydrochloride salt of Formula 1A) than with the less nucleophilic water introduced with the aqueous solution of Formula 1 or 1A.

This reaction to prepare the compound of Formula 14 using an aqueous solution of a compound of Formula 1 or 1A is performed in a similar manner to the procedure for using a compound of Formula 1 or 1A in the solid form. The order of addition of the reactants is similar to that discussed previously. When the acyl imidazole intermediate formation is complete, optionally a small quantity of water is added to hydrolyze any excess N,N'-carbonyldiimidazole (0.26 mole equivalent) and prevent side reactions. After the water quench of excess N,N'-carbonyldiimidazole at 20° C. for 1 hour, a concentrated aqueous solution of a compound of Formula 1 or 1A (about 50 M) or a slurry of a compound of Formula 1 or 1A in water is added dropwise. The reaction between the compound of Formula 1 or 1A and the intermediate of Formula 16 in aqueous acetonitrile usually takes 12 to 24 hours to complete. See synthesis Examples 12, 13, 14 and 15.

The aqueous solution of a compound of Formula 1 or 1A is prepared by adding water to the dry solid or is directly prepared in the procedure discussed below Scheme 1. The compound of Formula 15 was prepared according to the procedure of F. Feist in *Justus Liebigs Annalen der Chemie* 1932, 496, 99-122.

Another alternative procedure for the preparation of a compound of Formula 14 using the acid chloride of the compound of Formula 15 and the compound of Formula 1 is described in Example 7 of WO 2009/025983.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets and "br" means broad.

Example 1

Preparation of 2-amino-N-(2,2,2-trifluoroethyl)acetamide hydrochloride

N,N-Carbonyldiimidazole (8.2 g, 50.5 mmol) was added to a slurry of N-[(phenylmethoxy)carbonyl]glycine (10 g, 47.8 mmol) in iso-propyl acetate (100 mL) over 14 mins. The resulting solution was stirred for about 1 hr and then triethylamine (4.84 g, 47.8 mmol) was added followed by portionwise addition of trifluoroethylamine hydrochloride (6.8 g, 50.2 mmol) over 25 mins keeping the temperature below 30° C. The slurry was treated with water (50 mL) and iso-propyl acetate (25 mL). The resulting biphasic mixture was allowed to settle and the phases were separated. The aqueous layer was extracted with iso-propyl acetate (2×25 mL). The combined organic phases were washed with 1 N hydrochloric acid (50 mL), water (50 mL), saturated aqueous sodium bicarbonate (50 mL), brine (50 mL) and then dried over sodium sulfate (25 g) overnight. The slurry was filtered and the residue washed with iso-propyl acetate (30 mL).

10% Palladium on carbon (1.00 g) was added to the combined wash and filtrate and placed under a hydrogen atmosphere (balloon). After approximately 2 hours, the reaction slurry was heated to 50° C. and hydrogenated for approximately 4 hours. The reaction mixture was placed under a nitrogen atmosphere, cooled to room temperature and then filtered through a Celite® pad (15 g) wetted with iso-propyl acetate. The residue was rinsed with iso-propyl acetate (30 mL). The combined filtrate and rinse was treated with hydrogen chloride gas until the pH of the mixture was 1-2 by pH indicator paper, then nitrogen was bubbled through the slurry at 30-35° C. until the pH was 4-6 by pH indicator paper. The slurry was cooled to <5° C. and filtered. The residue was rinsed with iso-propyl acetate (20 mL) and dried in a vacuum oven at 60° C. to give the title compound as a gray solid (7.75 g, 84% yield).

Example 2

Preparation of phenylmethyl N-[2-oxo-2-[(2,2,2-trifluoroethyl)amino]ethyl]carbamate N,N-Carbonyldiimidazole (38.72 g, 0.2328 mol) was added to a slurry of N-[(phenylmethoxy)carbonyl]glycine (50 g, 0.239 mol) in ethyl acetate (350 mL) over 5 mins. The resulting solution was stirred for 65 minutes, then trifluoroethylamine hydrochloride (32.9 g, 0.24 mol) was added in portions keeping the temperature at 22° C. The reaction mixture was stirred for 17 hrs, then quenched with water (250 mL) and extracted with ethyl acetate (150 mL). The resulting biphasic mixture was allowed to settle and the phases were separated. The organic phase was washed twice with 1 N hydrochloric acid (100 mL each) and dried over magnesium sulfate (20 g) overnight. The slurry was filtered and the residue washed with 4 portions of ethyl acetate (50 mL, 100 mL, 100 mL, 50 mL). The washes and the filtrate were combined and concentrated to a solid. The solid was dried in a vacuum oven at 40° C. to give the title compound as a white solid (54.1 g, 78% yield).

1H NMR (DMSO-d$_6$): 8.55 (tr, J=6.4 Hz, 1H), 7.53 (tr, J=6.1 Hz, 1H), 7.43-7.22 (m, 5H), 5.04 (s, 2H), 4.01-3.79

(m, 2H), 3.68 ppm (d, J=6.1 Hz, 2H); $^{19}$F-NMR (DMSO-d6): −70.76 ppm (tr, J=10.1 Hz).

Example 3

A Second Preparation of
2-amino-N-(2,2,2-trifluoroethyl)acetamide
hydrochloride

A solution of tert.-butoxycarbonylglycine (285.7 g, 1.63 mol) in ethyl acetate (1140 mL) was added over about 1 hr to a slurry of N,N-carbonyldiimidazole (264.5 g, 1.63 mol) in ethyl acetate (570 mL) at ambient temperature. The reaction mixture was stirred for 1 hour and then 2,2,2-trifluoroethylamine hydrochloride (239.5 g, 1.77 mol) was added in portions over about 15 mins. The slurry was stirred for 5 hours at ambient temperature and then 1 N hydrochloric acid (860 mL) is added. The biphasic mixture was allowed to settle, and the phases were separated. The organic phase was consecutively washed with 1N hydrochloric acid (860 mL) and 5% sodium carbonate aqueous solution (860 mL), and then dried over magnesium sulfate and filtered. The filter cake was rinsed with ethyl acetate (200 mL). Hydrogen chloride gas (217 g, 5.95 mol) was bubbled through the combined filtrates at 20 to 37° C. over 2 hours. The resulting slurry was sparged with nitrogen and filtered. The residue was washed twice with ethyl acetate (500 mL each) and then dried in a vacuum oven at 60° C. to give the title compound as a white solid (235.5 g, 75% yield).

Example 4

A Third Preparation of
2-amino-N-(2,2,2-trifluoroethyl)acetamide
hydrochloride

Step A: Preparation of N-[2-oxo-2-[(2,2,2-trifluoroethyl)amino]ethyl]carbamic acid 1,1-dimethylethyl ester N,N-carbonyldiimidazole (8.87 g, 54.7 mmol) was added to a solution of N-tert-butoxycarbonylglycine (19 g, 57.1 mmol) in anhydrous ethyl acetate (50 ml) over 2 mins. The reaction mixture was stirred for 33 mins, and then 2,2,2-trifluoroethylamine (5.1 mL, 63.5 mmol) was added over 12 mins. The resulting solution was stirred overnight at ambient temperature, and then quenched with 1 N hydrochloric acid (25 mL). The reaction mixture was allowed to settle and the phases were separated. The organic phase was washed three times with water (25 ml each), diluted with ethyl acetate (10 mL), and dried over magnesium sulfate (5 g) for several hours. The slurry was filtered and the residue washed three times with ethyl acetate (10 mL). The filtrate and washes were combined and concentrated in-vacuo to give a white solid (12.7 g).
1H NMR (DMSO-d$_6$): 8.44 (tr, J=6.5 Hz, 1H), 7.01 (tr, J=6.2 Hz, 1H), 3.87-3.84 (m, 2H), 3.63-3.51 (d, J=6.4 Hz, 2H), 1.21-1.50 ppm (s, 9H); $^{19}$F-NMR (DMSO-d6): −70.75 ppm (tr, J=10 Hz).

Step B: Preparation of
2-amino-N-(2,2,2-trifluoroethyl)acetamide
hydrochloride

A portion of the product of Example 4, Step A (11.7 g) was diluted with ethyl acetate (50 mL) and treated with hydrogen chloride gas at 18-35.5° C. until the starting material was consumed. The resulting slurry was cooled to 0-5° C., stirred for approximately 1 hour at that temperature, and then filtered. The residue was washed twice with ethyl acetate (20 ml each) and dried in a vacuum oven at 60° C. to give the title compound as a white solid (7.22 g, 66% yield).
1H NMR (DMSO-d$_6$): 9.24 (tr, J=6.2 Hz, 1H), 8.3 (s, 3H), 4.11-3.89 (m, 2H), 3.64 (s, 2H), 1.21-1.50 ppm (s, 9H); $^{19}$F-NMR (DMSO-d6): −70.69 ppm (tr, J=10.1 Hz).

Step B1 Preparation of
2-amino-N-(2,2,2-trifluoroethyl)acetamide
hydrochloride

Hydrochloric acid (37 wt %, 2.1 mL, 25.6 mmol) was added in two portions to a mixture of N-[2-oxo-2-[(2,2,2-trifluoroethyl)amino]ethyl]carbamic acid 1,1-dimethylethyl ester (2.03 g, 7.9 mmol) in dichloromethane (10 mL) and water (0.7 mL). The resulting mixture was stirred at ambient temperature for about 2 hrs, then a solution of sodium carbonate (1.82 g) in water (6 g) was added. The cloudy mixture was acidified with 1N hydrochloric acid (21 mL) and diluted with 20 mL dichloromethane. The phases were separated and the aqueous phase concentrated to dryness on a rotary evaporator to give 3.16 g of the title compound as a white solid.

Example 5

Preparation of N-[2-oxo-2-[(2,2,2-trifluoroethyl)amino]ethyl]carbamic acid 1,1-dimethylethyl ester 2,2,2-trifluoroethylamine (2.1 mL, 26.1 mmol) was added dropwise to a slurry of 2,5-dioxo-3-oxazolidinecarboxylic acid 1,1-dimethylethyl ester (5.01 g, 24.8 mmol) in ethyl acetate (25 mL) at 3-6° C. The reaction was allowed to reach ambient temperature and stir overnight. The resultant slurry was diluted with ethyl acetate (35 mL) and washed successively with 5 wt % sodium carbonate (10 mL) and twice with water (10 mL each). The organic phase was dried over magnesium sulfate (5 g) and filtered via Buchner funnel. The residue on the funnel was washed twice with ethyl acetate (10 mL each) and the wash combined with the original filtrate. The combined organic phases were concentrated under vacuum and dried in a vacuum oven at 35° C. under a light nitrogen purge to give the title compound as a white solid (5.76 g, 90.8% yield).

Example 6

A Fourth Preparation of
2-amino-N-(2,2,2-trifluoroethyl)acetamide
hydrochloride

Triethylamine (11.67 g, 115 mmol) was added to a solution of tert.-butoxycarbonylglycine (20 g, 114 mol) in dichloromethane (110 mL) at <10° C. in one portion followed by addition of iso-butylchloroformate (15.75 g, 115 mmol) over 8 mins. The reaction mixture was allowed to stir for about 3.3 hrs at 10° C., then a solution of trifluoroethylamine (17 g, 171.6 mmol) and triethylamine (12.7 g, 122.5 mmol) in dichloromethane (72 mL) was added dropwise over 7 mins. The reaction mixture was stirred for about 2 hrs then quenched with 1 N hydrochloric acid (60 mL). The biphasic mixture was allowed to settle, and the phases were separated. The organic phase was consecutively washed with 1 N hydrochloric acid (60 mL) and 5% sodium carbonate aqueous solution (60 mL), and then dried over sodium sulfate and filtered. The filter cake was rinsed with ethyl acetate (30 mL) and the filtrate concentrated in vacuo. Ethyl acetate (50 mL) was added to the residue and the solution concentrated to an oil (23.81 g). The residue was redissolved in ethyl acetate (150 mL) and treated with hydrogen chloride gas at 35-41° C. until the GC analysis indicated completion of the deprotection reaction. The resulting slurry was sparged with nitrogen and filtered. The residue was washed twice with ethyl acetate (20 mL each) and dried in a vacuum oven at 60° C. to give the title compound as a white solid (8.9 g, 41% yield).

Example 7

Preparation of 2-amino-N-(2,2,2-trifluoroethyl)acetamide trifluoroacetate

A solution of trifluoroacetic acid (4.8 mL, 61.7 mmol) in dichloromethane (22 ml) was added to a slurry of N-[2-oxo-2-[(2,2,2-trifluoroethyl)amino]ethyl]carbamic acid 1,1-dimethylethyl ester (11.97 g, 46.7 mmol) in dichloromethane (50 mL) over 23 min at room temperature. The solution was heated to 39° C. and kept at that temperature for about 2 hrs. The solution was allowed to cool to ambient temperature then trifluoroacetic acid (4.8 mL, 61.7 mmol) was added and the hazy reaction mixture allowed to stir overnight. The reaction mixture was cooled to 0-5° C., kept at that temperature for 70 mins and then filtered via Büchner funnel to give a colorless gelatinous residue. The residue was washed with dichloromethane (1×40 mL, 1×15 mL) and then dried in a vacuum oven at 35° C. under a light nitrogen purge to give the title compound as a white sticky solid (6.08 g, 39.4%).

$^1$H NMR (DMSO-d$_6$): 9.13 (tr, J=6.3 Hz, 1H), 8.19 (s, 3H), 4.14-3.85 (m, 2H), 3.68 (s, 2H), $^{19}$F-NMR (DMSO-d$_6$): −70.83 ppm (tr, J=10 Hz), −74.93 (s).

Example 8

A Fifth Preparation of 2-amino-N-(2,2,2-trifluoroethyl)acetamide hydrochloride

Step A: Preparation of 2-chloro-N-(2,2,2-trifluoroethyl)acetamide

A solution of chloroacetyl chloride (60.8 g, 0.52 mol) in ethyl acetate (120 mL) was added to a pre-cooled (−5 to 0° C.) biphasic mixture of trifluoroethylamine (47.6 g, 0.48 mol) in anhydrous ethyl acetate (360 mL) and potassium carbonate (33.2 g, 0.24 mol) in water (120 mL) over 35 min. The reaction mixture was stirred for 60 min at that temperature. The reaction mixture was allowed to settle and the phases were separated. The organic phase was washed with water and concentrated under vacuum to give an oil. Methanol was added to dissolve the oil and the solution was concentrated under vacuum to a colorless oil which crystallized on cooling to a white solid (89.6 g).

$^1$H NMR (DMSO-d$_6$): 8.89 (bs, 1H), 4.17 (s, 2H), 3.91-3.99 (m, 2H).

Step B: Preparation of 2-[bis(phenylmethyl)amino]-N-(2,2,2-trifluoroethyl)acetamide A portion of the product of Example 7, Step A (40.0 g, 0.23 mol) was dissolved in methanol (300 mL) and added to a pressure reactor (Parr model 4540, 600 mL, Hasteloy C) along with dibenzylamine (39.5 g, 0.19 mol) and triethylamine (22.4 g, 0.22 mol). The reactor was flushed with nitrogen and sealed, then heated to 85° C. and held for 23 hours at that temperature. The reactor was cooled to ambient temperature and the crude reaction product was concentrated under vacuum to a red viscous oil which was redissolved in methylene chloride (400 mL). The solution was washed twice with water (450 mL total) and concentrated under vacuum to an amber oil which crystallized on cooling (63.5 g).

$^1$H NMR (DMSO-d$_6$): 8.38 (tr, 1H), 7.30-7.43 (m, 10H), 3.85-4.0 (m, 2H), 3.63 (s, 4H), 3.07 (s, 2H).

Step C: Preparation of 2-amino-N-(2,2,2-trifluoroethyl)acetamide hydrochloride

A portion of the product of Example 7, Step B (12.0 g) was dissolved in methanol (300 mL) and added to a pressure reactor (Parr model 4540, 600 mL, Hasteloy C) along with 5% palladium on carbon (0.6 g) catalyst. The reactor was flushed with nitrogen and then with hydrogen, and heated to 70° C. under 100 psi of hydrogen pressure until the hydrogen uptake ceased (3 hr). The reactor was cooled and flushed with nitrogen, then the crude reaction product was filtered through a bed a Celite® filter aid to remove the catalyst and the cake washed with methanol. The solvent and toluene by-product were removed by distillation, leaving an amber oil (5.45 g, 89% product by GC).

The crude oil product from two runs of the above hydrogenolysis (10.9 g total) was diluted with ethyl acetate (50 mL) and treated with hydrogen chloride gas at ambient temperature until the starting material was consumed. The resulting slurry was filtered and the solid was washed with ethyl acetate (20 mL) and dried on the filter under a blanket of nitrogen to give the title compound as a white solid (10.0 g).

$^1$H NMR (DMSO-d$_6$): 9.24 (tr, J=6.2 Hz, 1H), 8.3 (s, 3H), 4.11-3.89 (m, 2H), 3.64 (s, 2H); $^{19}$F-NMR (DMSO-d6): −70.69 ppm (tr, J=10.1 Hz).

Example 9

Preparation of 1-[4-(1H-imidazole1-ylcarbonyl)-1-naphthalenyl]ethanone

1H-Imidazole (1.17 g, 17.2 mmol) was added to a solution of 4-acetyl-1-naphthalenecarbonylchloride (2.01 g, 8.6 mmol) in dichloromethane (35 mL). The resulting slurry was stirred at ambient temperature for 11.5 hrs then cooled to 0° C. with an ice/water bath. Cold water (35 mL) was added and the reaction mixture transferred to a separatory funnel. The phases were separated, and the organic phase was washed with water (35 mL) and dried over magnesium sulfate. The slurry was filtered and the filtrate concentrated under vacuum to give the title compound as an orange oil.

$^1$H NMR (CDCl$_3$): 8.63-8.60 (m, 1H), 7.97-7.91 (m, 3H), 7.72-7.60 (m, 3H), 7.51 (tr, 1H, J=1.4 Hz), 7.18-7.17 (m, 1H), 2.80 (s, 3H).

Example 10

Preparation of 4-acetyl-N-[2-oxo-2-[(2,2,2-trifluoroethyl)amino]ethyl]-1-naphthalenecarboxamide 4-Acetyl-1-naphthalenecarboxylic acid (680 g, 3.14 mol) was added in five portions over 1 hour to a slurry of N,N-carbonyldiimidazole (505 g, 3.11 mol) in anhydrous acetonitrile (2720 mL) at ambient temperature. The solution was stirred for 2.5 hrs and then warmed to 35° C. 2-Amino-N-(2,2,2-trifluoroethyl)acetamide (530 g, 3.73 mol) was then added in five portions over 30 mins. The reaction mixture was allowed to stir for 2 hours at 35-40° C., then cooled and allowed to stir overnight at ambient temperature. The resulting slurry was treated with water (5540 mL) over 40 mins, followed by addition of a 1 N hydrochloric acid solution (5440 mL) over 30 mins. The reaction mixture was cooled to 5° C., held at that temperature for 1 hour and then filtered. The residue was washed 3 times with water (1360 mL each) and dried in a vacuum oven at 60° C. under a nitrogen purge to give the title product as a white solid (1042.6 g, 88.8% yield).

$^1$H NMR (CD$_3$S(=O)CD$_3$): 8.95 (t, J=5.8 Hz, 1H), 8.72 (t, J=6.5 Hz, 1H), 8.55 (dd, J=6.5, 2 Hz, 1H), 8.37-8.33 (m, 1H), 8.13 (d, J=7.3 Hz, 1H), 7.70-7.60 (m, 3H), 4.07-3.95 (m, 4H), 2.75 (s, 3H).

Example 11

A Second Preparation of 4-acetyl-N-[2-oxo-2-[(2,2,2-trifluoroethyl)amino]ethyl]-1-naphthalenecarboxamide 4-Acetyl-1-naphthalenecarboxylic acid (675 g, 3.15 mol) was added in five portions over 32 mins to a slurry of N,N-carbonyldiimidazole (486 g, 3.00 mol) in anhydrous acetonitrile (2578 mL) at about 36° C. The solution was stirred for approximately 2 hrs at this temperature and then 2-amino-N-(2,2,2-trifluoroethyl)acetamide hydrochloride (629 g, 3.27 mol) was added in five portions over 36 mins. The reaction mixture was allowed to stir overnight at 35° C. and then cooled to about 18° C. to initiate crystallization. The resulting slurry was warmed to 35° C. and then 1 N hydrochloric acid (3064 mL) was added over 90 mins, followed by addition of a solution of 50% sodium hydroxide (514.2 g) in water (7356 mL) over 81 mins. The reaction mixture was cooled to about 18° C., held at that temperature for 30 mins and then filtered The residue was washed 3 times with water (700 mL each) and dried in a vacuum oven at 60° C. under a nitrogen purge to give the title product as a white solid (988.6 g, 87.7% yield).

Example 12

A Third Preparation of 4-acetyl-N-[2-oxo-2-[(2,2,2-trifluoroethyl)amino]ethyl]-1-naphthalenecarboxamide 4-Acetyl-1-naphthalenecarboxylic acid (50 g, 0.2273 mol) was added in portions to a slurry of N,N-carbonyldiimidazole (39.76 g, 0.2388 mol) in anhydrous acetonitrile (200 mL) at 30° C. The solution was stirred for 2 hrs at 30° C. and then cooled to 20° C. Water (1.06 g, 58.8 mmol) was added to the mixture and it was stirred for 1 hr. A solution of 2-amino-N-(2,2,2-trifluoroethyl)acetamide hydrochloride (45.98 g, 0.2388 mol) in water (21.5 g) was then added over 1 hr at 19-20° C. The reaction mixture was allowed to stir for 17 hours. To the resulting slurry, water (100 mL) was added, followed by addition of a solution of sodium carbonate (24.1 g, 0.2274 mol) in water (350 mL) over 25 mins and water (350 mL) over 22 mins. The reaction mixture was stirred at 20-25° C. for 6.5 hrs and filtered. The residue was washed 3 times with water (100 mL each) and dried in a vacuum oven at 50-60° C. under a nitrogen purge to give the title product as a white solid (72.3 g, 86.1% yield).

Example 13

A Fourth Preparation of 4-acetyl-N-[2-oxo-2-[(2,2,2-trifluoroethyl)amino]ethyl]-1-naphthalenecarboxamide Anhydrous acetonitrile (40 mL) was added to 4-acetyl-1-naphthalenecarboxylic acid (10.0 g, 46.5 mmol) and N,N-carbonyldiimidazole (7.62 g, 46.5 mmol). The solution was stirred for 5.75 hrs at 25° C., and then heated to 30° C. A solution of 2-amino-N-(2,2,2-trifluoroethyl)acetamide hydrochloride (9.84 g, 50.8 mmol) in water (4.32 g) was added over 6 mins. The reaction mixture was allowed to stir for 16.3 hours at 30° C. and then cooled to 20° C. To the resulting slurry, water (20 mL) was added, followed by addition of a solution of sodium carbonate (9.86 g, 93 mmol) in water (140 mL) over about 1 hr. The reaction mixture was stirred at 20-25° C. overnight, held at 0-8° C. for 2.25 hrs and then filtered. The residue was washed 3 times with water (20 mL each) and dried in a vacuum oven at 50° C. under a nitrogen purge to give the title product as an off-white solid (14.83 g, 87.8% yield).

Example 14

A Fifth Preparation of 4-acetyl-N-[2-oxo-2-[(2,2,2-trifluoroethyl)amino]ethyl]-1-naphthalenecarboxamide 4-Acetyl-1-naphthalenecarboxylic acid (10.0 g, 46.5 mmol) was added to a slurry of N,N-carbonyldiimidazole (8.21 g, 50.1 mmol) in anhydrous acetonitrile (40 mL). The solution was stirred for 1.3 hrs at ambient temperature. Water (0.2 mL, 11.1 mmol) was added and the solution stirred for 30 mins. A solution of 2-amino-N-(2,2,2-trifluoroethyl)acetamide sulfate (11.25 g, 54.8 mmol) in water (22.6 g) was prepared and filtered to remove insolubles and then added over 3 mins to the reaction mixture. The reaction mixture was allowed to stir for 21.3 hrs at 21-23° C. To the resulting slurry, water (20 mL) was added, followed by addition of a solution of sodium carbonate (9.82 g, 92.7 mmol) in water (140 mL) over 15 minutes. The reaction mixture was cooled and stirred at 0-5° C. for 2.3 hrs and then filtered. The residue was washed 3 times with water (20 mL each) and dried in a vacuum oven at 45° C. under a slight nitrogen purge to give the title compound as an off-white solid (12.6 g, 76.9% yield).

Example 15

A Sixth Preparation of 4-acetyl-N-[2-oxo-2-[(2,2,2-trifluoroethyl)amino]ethyl]-1-naphthalenecarboxamide 4-Acetyl-1-naphthalenecarboxylic acid (10.0 g, 46.5 mmol) was added to a slurry of N,N-carbonyldiimidazole (8.22 g, 50.2 mmol) in anhydrous acetonitrile (40 mL). The solution was stirred for 2 hrs 10 mins at 19 to 21° C. Water (0.2 mL, 11.1 mmol) was added and the solution stirred for 1 hr. A solution of 2-amino-N-(2,2,2-trifluoroethyl)acetamide (9.03 g, 55.1 mmol) in water (16.5 g) was prepared and filtered to remove insolubles. The solid residue on the filter was washed with water (1.58 g) and washings combined with the filtered aqueous solution of 2-amino-N-(2,2, 2-trifluoroethyl)acetamide. The aqueous solution of 2-amino-N-(2,2,2-trifluoroethyl)acetamide was added to the reaction mixture containing the acylimidazole intermediate over 12 mins. The reaction mixture was allowed to stir for 20.6 hours at ambient temperature. To the resulting slurry, water (20 mL) was added, followed by dropwise addition of a solution of sodium carbonate (4.91 g, 46.3 mmol) in water (70 mL) over 16 mins and water (70 mL) over 10 mins. The reaction mixture was cooled and stirred at 2-7° C. for 2.5 hrs and then filtered. The residue was washed 3 times with water (20 mL each) and dried in a vacuum oven at 45° C. under a slight nitrogen purge to give the title compound as an off-white solid (13.83 g, 84.4% yield).

Example 16

Stability comparison for free base and salts of 2-amino-N-(2,2,2-trifluoroethyl)acetamide The 2-amino-N-(2,2,2-trifluoroethyl)acetamide free base unexpectedly showed weight gain upon exposure to the ambient atmosphere, whereas the corresponding hydrochloride salt did not. This result was not expected as hydrochloride salts of amines are quite frequently hydroscopic. To further characterize the stability of the free amine and salts of 2-amino-N-(2,2,2-trifluoroethyl)acetamide the following experiments were performed. Samples of the free amine and salts were exposed to air in the laboratory for a period of time. Weight lain or loss compared to the original sample was determined

| Salt | % Weight gain (loss) | Time [days] in ambient atmosphere |
| --- | --- | --- |
| Free base | 4.65 | 3 |
| Hydrochloride | (0.09) | 2 |
| Trifluoroacetate | (0.22) | 2.6 |
| Methanesulfonate | (0.76) | 5 |

What is claimed is:
1. A method for preparing a salt having Formula 1A

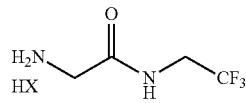

1A wherein X is Cl
comprising
(A1) i) forming a reaction mixture by a) at a temperature between at least about 15° C. and no more than about 40° C., contacting in isopropyl acetate, a compound of Formula 8

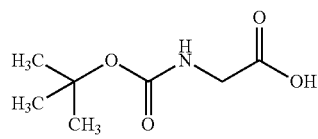

8 with N,N'-carbonyldiimidazole, wherein the N,N'-carbonyldiimidazole reacts with the compound of Formula 8 to form a base derived from the N,N'-carbonyldiimidazole and an intermediate of Formula 9,

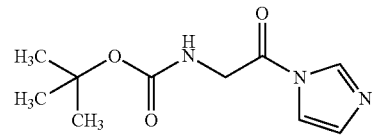

9 and then, after 1-2 hours,
b) adding to the reaction mixture a salt having Formula 3

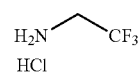

3 which reacts with the intermediate of Formula 9 in the presence of the base derived from the N,N'-carbonyldiimidazole to form an intermediate of Formula 7

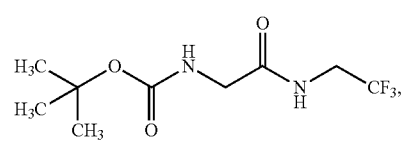

7 in the reaction mixture; and
ii) then washing the intermediate of Formula 7 in the reaction mixture by adding 1N HCl and removing water by azeotropic drying to produce a solution of intermediate of Formula 7 in isopropyl acetate; and
(B1) contacting the solution of intermediate of Formula 7 in isopropyl acetate, from step (A1) ii) with an acid of Formula 5

HX                                                        5 to provide the compound of Formula 1A.
2. The method of claim 1 wherein in step (A1) the compound of Formula 8 and the salt having Formula 3 and the N,N'-carbonyldiimidazole are contacted in the presence of an additional base.
3. The method of claim 2 wherein the additional base is triethylamine.
4. The method of claim 1 wherein the hydrogen chloride is added as hydrogen chloride gas.
5. The method of claim 3 wherein the hydrogen chloride is added as hydrogen chloride gas.

* * * * *